US011462328B2

United States Patent
Mazumder et al.

(10) Patent No.: US 11,462,328 B2
(45) Date of Patent: Oct. 4, 2022

(54) METHOD AND SYSTEM FOR INJURY RISK PREDICTION AND CORRECTIVE ACTION FOR HIGH CONTACT TYPE ACTIVITY

(71) Applicant: Tata Consultancy Services Limited, Mumbai (IN)

(72) Inventors: Oishee Mazumder, Kolkata (IN); Aniruddha Sinha, Kolkata (IN); Kingshuk Chakravarty, Kolkata (IN); Debatri Chatterjee, Kolkata (IN)

(73) Assignee: Tata Consultancy Services Limited, Mumbai (IN)

(*) Notice: Subject to any disclaimer, the term of this patent is extended or adjusted under 35 U.S.C. 154(b) by 975 days.

(21) Appl. No.: 16/208,095

(22) Filed: Dec. 3, 2018

(65) Prior Publication Data

US 2019/0172585 A1 Jun. 6, 2019

(30) Foreign Application Priority Data

Dec. 1, 2017 (IN) .............................. 201721043259

(51) Int. Cl.
*G16H 50/30* (2018.01)
*G16H 50/50* (2018.01)
(Continued)

(52) U.S. Cl.
CPC ............. *G16H 50/30* (2018.01); *G06F 30/20* (2020.01); *G06T 17/00* (2013.01); *G16H 50/50* (2018.01)

(58) Field of Classification Search
CPC ........ G16H 50/30; G16H 30/20; G16H 50/50; G06T 17/00
See application file for complete search history.

(56) References Cited

U.S. PATENT DOCUMENTS

2010/0205008 A1* 8/2010 Hua ....................... G06Q 50/22
  705/3
2013/0244211 A1* 9/2013 Dowling ................ G16H 20/30
  434/247
(Continued)

FOREIGN PATENT DOCUMENTS

WO WO-2016161457 10/2016

OTHER PUBLICATIONS

Hang Xu et al.; "An improved OpenSim gait model with multiple degrees of freedom knee joint and knee ligaments"; Computer Methods in Biomechanics and Biomedical Engineering, 2015, vol. 18, No. 11, 1217-1224 (Year: 2015).*

(Continued)

*Primary Examiner* — Rehana Perveen
*Assistant Examiner* — Nupur Debnath
(74) *Attorney, Agent, or Firm* — Finnegan, Henderson, Farabow, Garrett & Dunner, LLP

(57) ABSTRACT

A system and method for risk prediction and corrective action for a contact type activity is provided. The method includes generating a personalized full body musculoskeletal model to depict the knee and ankle joint behavior of a subject during the contact type activity. Various contact type activities are simulated using the personalized full body musculoskeletal model. Injury biomarkers and their parameters based on the contact type activities are identified, parameters are indicative of risk of injury to participating muscle groups said activity. Based on the injury biomarkers, optimal muscle co-activation parameters are analyzed by a neuro-muscular controller, to adapt the participating muscle groups for providing the correction action against the predicted risk of injury. Said optimal muscle co-activation parameters are indicative of muscle synergy during the contact type activity.

16 Claims, 9 Drawing Sheets

(51) Int. Cl.
*G06F 30/20* (2020.01)
*G06T 17/00* (2006.01)

(56) References Cited

U.S. PATENT DOCUMENTS

| | | | | |
|---|---|---|---|---|
| 2016/0070873 A1* | 3/2016 | Huster | G16H 20/40 | |
| | | | | 700/90 |
| 2017/0164876 A1* | 6/2017 | Hyde | A61B 5/389 | |
| 2017/0303849 A1* | 10/2017 | De Sapio | G16H 20/30 | |

OTHER PUBLICATIONS

Kundu et al.; "Trajectory Generation for Myoelectrically Controlled Lower Limb Active Knee Exoskeleton"; 2014 IEEE (Year: 2014).*

Oishee Mazumder et al.; "Modeling, Simulation and Control Architecture for Lower Limb Active Exoskeleton"; AIR '15, Jul. 2-4, 2015 (Year: 2015).*

S. G. McLean et al.; "Development and Validation of a 3-D Model to Predict Knee Joint Loading During Dynamic Movement"; vol. 125, (Year: 2003).*

Ajay Seth et al.; "OpenSim: a musculoskeletal modeling and simulation framework for in silico investigations and exchange"; Procedia IUTAM. 2011 (Year: 2011).*

Timothy E. Hewett et al.; "Biomechanical Measures of Neuromuscular Control and Valgus Loading of the Knee Predict Anterior Cruciate Ligament Injury Risk in Female Athlete;" (Year: 2005).*

Hossein Rouhani et al. "PID Controller Design for FES Applied to Ankle Muscles in Neuroprosthesis for Standing Balance"; Frontier Neuroscience, Jun. 20, 2017 (Year: 2017).*

Hewett, T.E. et al. (Nov. 2016) "Mechanisms, Prediction, and Prevention of ACL Injuries: Cut Risk with Three Sharpened and Validated Tools," *J Orthop Res*, vol. 34, No. 11; pp. 1843-1855.

* cited by examiner

METHOD AND SYSTEM FOR INJURY RISK PREDICTION AND CORRECTIVE ACTION FOR HIGH CONTACT TYPE ACTIVITY

PRIORITY CLAIM

This U.S. patent application claims priority under 35 U.S.C. § 119 to: India Application No. 201721043259, filed on Dec. 1, 2017. The entire contents of the aforementioned application are incorporated herein by reference.

TECHNICAL FIELD

The embodiments herein generally relate to injury risk prediction and adaption, and more particularly to, a system and method for injury risk prediction and corresponding corrective action for high contact type activity.

BACKGROUND

High contact type activities are those that can produce a high impact on contact during an activity. High demand sports such as soccer, basketball and football fall in the category of high contact type activities. Anterior cruciate ligament (ACL) injuries are the most predominant form of knee injuries faced by athletics participating in high demand sports.

Typically, most of ACL injuries are non-contact type, and are sustained due to side cutting maneuvers or when landing from a jump. Single leg landing is one such athletic maneuver, associated with most high demand sports, which has one of the highest risks of ACL injury. ACL injuries cause devastating consequences to subjects' quality of life along with inducing a lifetime financial burden to society. According to an estimate, lifetime financial burden of said injuries to society is estimated to be around US$7.6 billion annually when treated with ACL reconstruction and US$17.7 billion when treated with rehabilitation. Even with ACL reconstructions, subjects usually have abnormal strength, proprioception, balance, and Neuro-muscular control patterns as well as increased risks for re-injury in post-reconstructed ACLs.

In addition to the above mentioned, the inventors have recognized certain technical problems associated with currently available solutions pertaining to injuries sustained during high contact type activity. For example, the current solutions have little or no capability to observe such injuries during in-vivo testing. For preventing sports related injuries, understanding of injury mechanisms and identification of risk factors along with development and evaluation of injury prevention strategies are required. The current solutions lack understanding and identification of the injury mechanisms and risk factors for ACL injury. Consequently current ACL injury prevention solutions have limitations that prevent them from being effective.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides methods and systems for injury risk prediction and corresponding corrective action for high contact type activity. The method includes generating a personalized full body musculoskeletal model to depict the knee and ankle joint behavior of a subject during the contact type activity, via one or more hardware processors. Further, the method includes simulating one or more contact type activities using the personalized full body musculoskeletal model, via the one or more hardware processors. Furthermore, the method includes identifying a plurality of injury biomarkers based on the one or more contact type activities, via the one or more hardware processors. Also, the method includes analyzing a plurality of parameters indicative of risk of injury to a plurality of participating muscle groups during contact type activity calculated with respect to the plurality of injury biomarkers to predict said risk of injury, via the one or more hardware processors. Moreover, the method includes generating, based on at least the plurality of injury biomarkers, a plurality of optimal muscle co-activation parameters by a neuro-muscular controller, to adapt the plurality of participating muscle groups for providing the correction action against the predicted risk of injury, via the one or more hardware processors. The plurality of optimal muscle co-activation parameters are indicative of muscle synergy during the one or more contact type activities.

In another aspect, a system for injury risk prediction and corresponding corrective action for high contact type activity is provided. The system includes one or more memories; and one or more hardware processors, the one or more memories coupled to the one or more hardware processors, wherein the one or more hardware processors are capable of executing programmed instructions stored in the one or more memories to generate a personalized full body musculoskeletal model to depict the knee and ankle joint behavior of a subject during one or more contact type activity. Furthermore, the one or more hardware processors are configured by the instructions to simulate the contact type activities using the personalized full body musculoskeletal model. Moreover, the one or more hardware processors are configured by the instructions to identify a plurality of injury biomarkers based on the one or more contact type activities. Also, the one or more hardware processors are configured by the instructions to analyze a plurality of parameters indicative of risk of injury to a plurality of participating muscle groups during the one or more contact type activities calculated with respect to the plurality of injury biomarkers to predict said risk of injury. Also, the one or more hardware processors are configured by the instructions to generate, based on at least the plurality of injury biomarkers, a plurality of optimal muscle co-activation parameters by a neuro-muscular controller, to adapt the plurality of participating muscle groups for providing the correction action against the predicted risk of injury, the plurality of optimal muscle co-activation parameters indicative of muscle synergy during the one or more contact type activity.

In yet another aspect, a non-transitory computer-readable medium having embodied thereon a computer program for executing a method for injury risk prediction and corresponding corrective action for high contact type activity is provided. The method includes generating a personalized full body musculoskeletal model to depict the knee and ankle joint behavior of a subject during one or more contact type activities, via one or more hardware processors. Further, the method includes simulating a one or more contact type activities using the personalized full body musculoskeletal model. Furthermore, the method includes identifying a plurality of injury biomarkers based on the one or more contact type activities. Also, the method includes analyzing a plurality of parameters indicative of risk of injury to a plurality of participating muscle groups during the one or more contact type activities calculated with respect to the plurality of injury biomarkers to predict said risk of injury. Moreover, the method includes generating, based on at least the plurality of injury biomarkers, a plurality of optimal muscle co-activation parameters by a neuro-muscular controller, to adapt the plurality of participating muscle groups for providing the correction action against the predicted risk of injury. The plurality of optimal muscle co-activation parameters are indicative of muscle synergy during the one or more contact type activity.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to reference like features and modules.

Figure 1A:
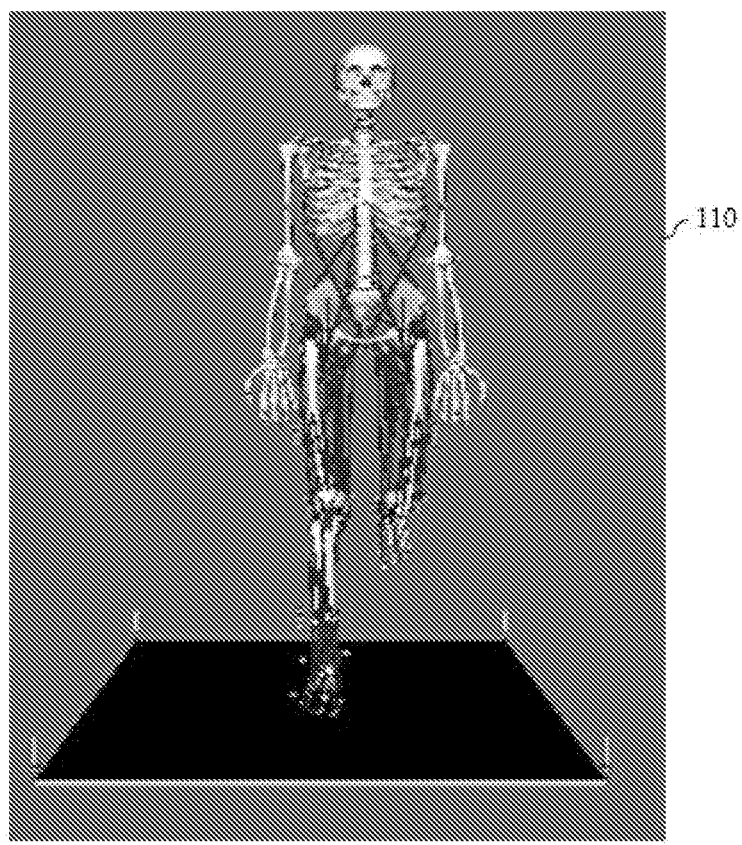
FIG. 1A illustrates an example musculoskeletal model developed to simulate single leg drop jump activity, in accordance with example embodiments of the present subject matter.

It should be appreciated by those skilled in the art that any block diagrams herein represent conceptual views of illustrative systems and devices embodying the principles of the present subject matter. Similarly, it will be appreciated that any flow charts, flow diagrams, and the like represent various processes which may be substantially represented in computer readable medium and so executed by a computer or processor, whether or not such computer or processor is explicitly shown.

DETAILED DESCRIPTION

High contact type activities are those that can produce a high impact on contact during an activity. High demand sports such as soccer, basketball and football fall in the category of high contact type activities. Anterior cruciate ligament (ACL) injuries are the most predominant form of knee injuries faced by athletics participating in high demand sports. Typically, most of ACL injuries are non-contact type, and are sustained due to side cutting maneuvers or when landing from a jump. Single leg landing is one such athletic maneuver, associated with most high demand sports, which has one of the highest risks of ACL injury.

Conventionally available solutions pertaining to ACL injuries have little or no capability to observe such injuries during in-vivo testing. For preventing sports related injuries, understanding of injury mechanisms and identification of risk factors along with development and evaluation of injury prevention strategies are required. The current solutions lack understanding and identification of the injury mechanisms and risk factors for ACL injury. Consequently current ACL injury prevention solutions have limitations that prevent them from being effective.

Various embodiments presented herein disclose system and method for injury risk prediction and corresponding corrective action for high contact type activity. The disclosed method and system combine motion analysis of the subject and musculoskeletal modelling techniques to provide estimates of muscle forces during a landing manoeuvres during the high contact type activity. The system facilitates neuromuscular coordination, analyze athletic performance, and estimate internal loading of the musculoskeletal system.

In an embodiment, the method includes designing a model for predicting chance of injury during contact type sports/exercise, and an optimal neuro-muscular controller to adjust muscle synergy so that the predicted injury can be reduced or avoided. The disclosed model for predicting the chance of said injury risk simulates various high contact type activities and determines effect of said activities on full body knee and ankle biomechanics. The embodiments identify potential injury biomarkers of said activities' injuries and determine the effect of said injury biomarkers on changing muscle activation of associated muscles. Based on said determination and biomechanical modeling, a neuro-muscular controller associated with the disclosed system adjusts the optimal synergistic muscle activation parameters to prevent the injury condition. Herein, it will be noted that the simulations of the said activity risks can also be used to identify the sources of pathological movement and establish a scientific basis for treatment planning. Additionally, the simulation of injury mechanism using neuro-muscular modelling is done to determine optimal and synergistic muscle activations that can be induced in athletic training to prevent the injury. An example of the musculoskeletal model developed in accordance with disclosed embodiment is illustrated and described further with reference to FIG. 1A.

Figure 1B:
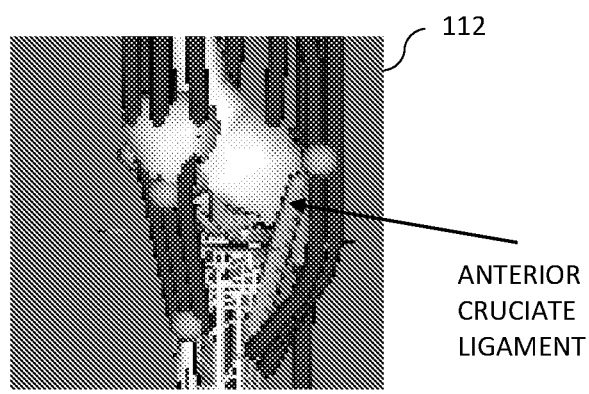
FIGS. 1B, 1C and 1D illustrate positioning of the additional ligaments in the knee joint region in the musculoskeletal model of FIG. 1A, in accordance with example embodiments of the present subject matter.
Figure 1C:
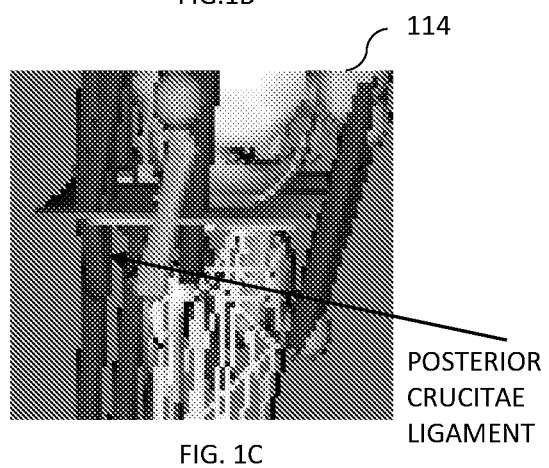
Figure 1D:
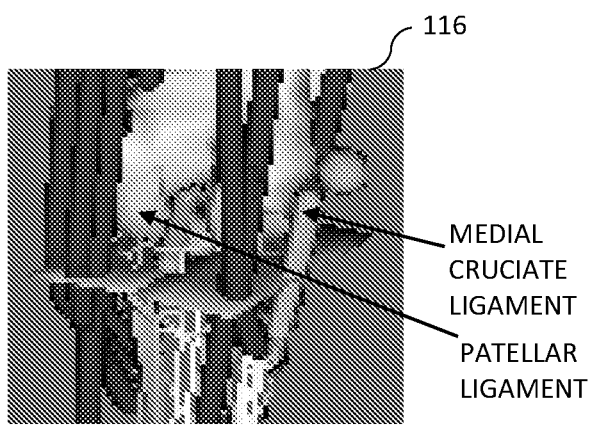

Referring to FIG. 1A, an example personalized full body musculoskeletal model 110 developed to simulate single leg drop jump activity is illustrated. For the brevity of description, the personalized full body musculoskeletal model may hereinafter be referred to as a model 110. Further, FIGS. 1B, 1C, and 1D illustrate expanded view of positioning of the additional ligaments in the knee joint region 112, 114, 116, respectively of the simulated model 110. For example FIG. 1B illustrates an anterior cruciate ligament, FIG. 1C illustrates a posterior cruciate ligament, and FIG. 1D illustrates a medial cruciate ligament and a patellar ligament.

The methods and systems are not limited to the specific embodiments described herein. In addition, the method and system can be practiced independently and separately from other modules and methods described herein. Each device element/module and method can be used in combination with other elements/modules and other methods.

The manner, in which the system and method for injury risk prediction and corresponding corrective action for high contact type activity shall be implemented, has been explained in details with respect to the FIGS. 2 through 8C. While aspects of described methods and systems for injury risk prediction and corresponding corrective action for high contact type activity can be implemented in any number of different systems, utility environments, and/or configurations, the embodiments are described in the context of the following exemplary system(s).

Figure 2:
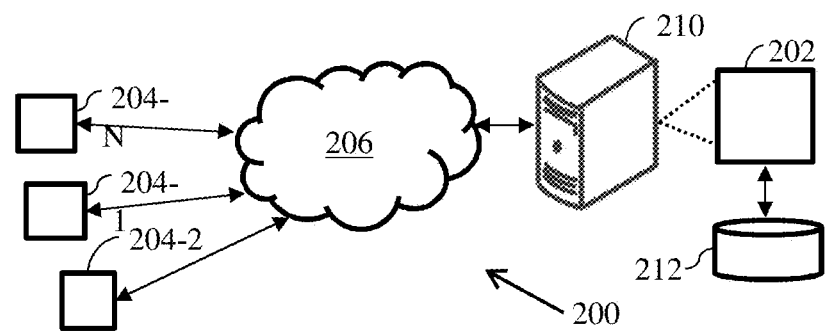
FIG. 2 illustrates a network implementation of a system for injury risk prediction and corresponding corrective action for high contact type activity, in accordance with an embodiment of the present subject matter.

Referring now to FIG. 2, a network implementation 200 of system 202 for injury risk prediction and corresponding corrective action for high contact type activity is illustrated, in accordance with an embodiment of the present subject matter. The system is adapted to develop a musculoskeletal model with enhanced knee joint anatomy, including 3 degrees of freedom (DoF) knee joint and 9 ligament bundles. Additionally, the system 202 is caused to simulate high contact type activities such as a drop jump exercise to induce an injury condition and subsequent analysis of muscle condition, joint kinematics and kinetics associated with risk of ACL injury. Further, the system 202 develops a neuromuscular controller which generates optimal muscle co-activation parameters to adapt the subject's body so that the chances of predicted injury is reduced or avoided.

Although the present subject matter is explained considering that the system 202 is implemented for injury risk prediction and corresponding corrective action for high contact type activity, it may be understood that the system 202 may not be restricted to any particular machine or environment. The system 202 can be utilized for a variety of domains where PPG signal quality assessment is to be determined. The system 202 may be implemented in a variety of computing systems, such as a laptop computer, a desktop computer, a notebook, a workstation, a mainframe computer, a server, a network server, a smart phone, a wearable device, and the like.

Herein, the system 202 may acquire an input data for modelling a personalized full body musculoskeletal model via devices and/or machines 204-1, 204-2 . . . 204-N, collectively referred to as devices 204 hereinafter. In an embodiment, the devices 204 may include high end motion measurement system such as VICON™ or equivalent optical marker based motion analysis, Ground Reaction force plate, myoelectric devices, and so on. In an embodiment, the devices 204 may be embodied in handheld electronic device, a mobile phone, a smartphone, a portable computer, a PDA, and so on. The devices 204 are communicatively coupled to the system 202 through a network 206, and may be capable of providing input data to the system 202.

In one implementation, the network 206 may be a wireless network, a wired network or a combination thereof. The network 306 can be implemented as one of the different types of networks, such as intranet, local area network (LAN), wide area network (WAN), the internet, and the like. The network 206 may either be a dedicated network or a shared network. The shared network represents an association of the different types of networks that use a variety of protocols, for example, Hypertext Transfer Protocol (HTTP), Transmission Control Protocol/Internet Protocol (TCP/IP), Wireless Application Protocol (WAP), and the like, to communicate with one another. Further, the network 206 may include a variety of network devices, including routers, bridges, servers, computing devices, storage devices, and the like.

In an embodiment, the system 202 may be embodied in the computing device 210. The system 202 may also be associated with a data repository 212 to store at least data required for modeling the personalized full body musculoskeletal model. Additionally or alternatively, the data repository 212 may be configured to store data and/or information generated during injury risk prediction and corresponding corrective action for high contact type activity. The repository 212 may be configured outside and communicably coupled to the computing device 210 embodying the system 202. Alternatively, the data repository 212 may be configured within the system 202. An example implementation of the system 202 for injury risk prediction and corresponding corrective action for high contact type activity is described further with reference to FIG. 3.

Figure 3:
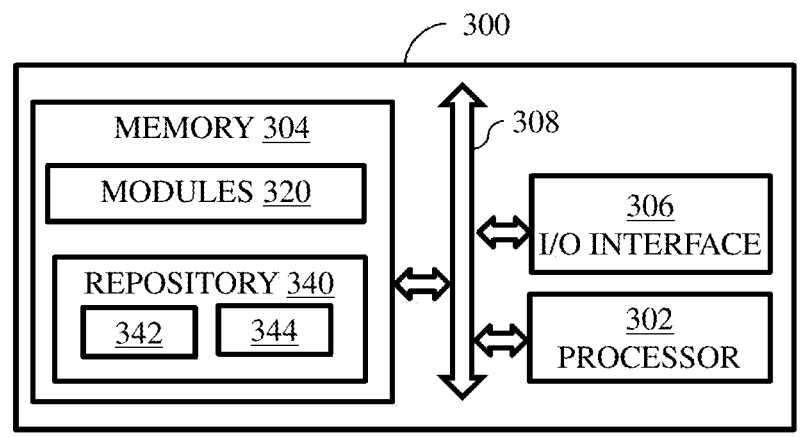
FIG. 3 illustrates a block diagram of a system for injury risk prediction and corresponding corrective action for high contact type activity, in accordance with an embodiment of the present subject matter.

FIG. 3 illustrates a block diagram of an exemplary system 300 for injury risk prediction and corresponding corrective action for high contact type activity, in accordance with an example embodiment. The system 300 may be an example of the system 202 (FIG. 2). In an example embodiment, the system 300 may be embodied in, or is in direct communication with the system, for example the system 202 (FIG. 2). The system 300 includes or is otherwise in communication with one or more hardware processors such as a processor 302, at least one memory such as a memory 304, and an I/O interface 306. The processor 302, memory 304, and the I/O interface 306 may be coupled by a system bus such as a system bus 308 or a similar mechanism.

The hardware processor 302 may be implemented as one or more microprocessors, microcomputers, microcontrollers, digital signal processors, central processing units, state machines, logic circuitries, and/or any devices that manipulate signals based on operational instructions. Among other capabilities, the processor 302 is configured to fetch and execute computer-readable instructions stored in the memory 304.

The I/O interface 306 may include a variety of software and hardware interfaces, for example, a web interface, a graphical user interface, and the like. The interfaces 306 may include a variety of software and hardware interfaces, for example, interfaces for peripheral device(s), such as a keyboard, a mouse, an external memory, a camera device, and a printer. Further, the interfaces 306 may enable the system 302 to communicate with other devices, such as web servers and external databases. The interfaces 306 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 306 may include one or more ports for connecting a number of computing systems with one another or to another server computer. The I/O interface 306 may include one or more ports for connecting a number of devices to one another or to another server.

The memory 304 may include any computer-readable medium known in the art including, for example, volatile memory, such as static random access memory (SRAM) and dynamic random access memory (DRAM), and/or nonvolatile memory, such as read only memory (ROM), erasable programmable ROM, flash memories, hard disks, optical disks, and magnetic tapes. In an embodiment, the memory 304 includes a plurality of modules 320 and a repository 340 for storing data processed, received, and generated by one or more of the modules 320. The modules 320 may include routines, programs, objects, components, data structures, and so on, which perform particular tasks or implement particular abstract data types. Additionally, the other modules 320 may include programs or coded instructions that supplement applications and functions of the system 300. The repository 340, amongst other things, includes a system database 342 and other data 344. The other data 344 may include data generated as a result of the execution of one or more modules in the modules 320. Herein, the memory for example the memory 304 and the computer program code configured to, with the hardware processor for example the processor 302, causes the system 300 to perform various functions described herein under.

As discussed above, for injury risk prediction and corresponding corrective action for high contact type activity, the system 300 is caused to generate a personalized full body musculoskeletal model of a subject. The personalized full body musculoskeletal model (hereinafter referred to as a musculoskeletal model) depicts the knee and ankle joint behaviour of the subject during the contact type activity. An example representation of a musculoskeletal model along with the knee and ankle joint behaviour of the subject is illustrated with reference to FIGS. 1A-1D.

In an example embodiment, the system 300 may utilize an OpenSim™ platform to generate the musculoskeletal model. In an embodiment, the system 300 is caused to improvise generic model, for example as the one generated by the OpenSim™ platform in terms of ligament placement and a modified 3DoF knee to facilitate a sliding motion. In an embodiment, musculoskeletal model includes at least 92 muscle actuators a 3 DoF knee with ligament connectivity, and 9 ligament bundles designed and placed with respect to anatomical constraints and bounds. In an example embodiment, a group of 9 different ligaments naming, ACL (anterior and posterior), PCL (anterior and posterior), Fibular Collateral ligament (lateral), Patella-femoral ligament and Tibial collateral ligament (anterior, intermediate and posterior) may be modelled to depict the knee and ankle joint behaviour during a high contact type activity, such as sports activity.

The system 300 simulates one or more contact type activities using the musculoskeletal model. For example the system 300 may be caused to simulate, by using the musculoskeletal model, a jump (for instance, a single leg drop jump) from a four different heights, ranging from 40 to 100 cm on a solid platform. In typical scenarios, unsupervised and sudden jump such as the one simulated herein may cause tear in ACL ligament. Herein, the purpose of said simulation is to induce an injury scenario during the high contact type activity.

Whether an injury has occurred or not is reflected by one or more injury biomarkers. In an embodiment, the system 300 identifies a plurality of injury biomarkers based on the one or more contact type activities. Examples of said injury biomarkers include, but are not limited to hip abduction angle, knee abduction angle, loading at knee joint, and so on. Said injury biomarkers can be calculated from forward and inverse dynamics. In an embodiment, the plurality of injury biomarkers are identified through inverse dynamics simulation of the musculoskeletal model. These parameters have been analyzed in OpenSim™ platform to check whether there is any chance of injury, incurred from the high contact type activity.

The system 300 analyzes a plurality of parameters indicative of risk of injury to a plurality of participating muscle groups of the subject during the contact type activity calculated with respect to the plurality of injury biomarkers so as to predict said risk of injury. In an embodiment, said plurality of parameters may include subject's muscle condition, joint kinematics and kinetics associated with said risk. In case of an ACL injury, the plurality of participating muscles groups includes quadriceps Hamstring, and Tibialis anterior and Gastrocnemius. Herein, a change in an activation function of participating muscles groups produce detectable changes in the plurality of injury biomarkers.

Once the system 200 predicts chances of injury, calculated with respect to specific injury biomarkers including hip abduction angle and knee loading, a neuro-muscular controller is designed, which adjusts muscle co-activation and synergy of two groups of participating muscles, namely Quadriceps: hamstring and gastrocnemius: Tibilias Anterior.

In an embodiment, the system 300 generates, based on at least the plurality of injury biomarkers, a plurality of optimal muscle co-activation parameters by a neuro-muscular controller, to adapt the plurality of participating muscle groups for providing the correction action against the predicted risk of injury. Herein, the plurality of optimal muscle co-activation parameters are indicative of muscle synergy during the contact type activity. For example, co-activation may refer to simultaneous contraction of agonist and antagonist muscle pair around a specific joint to provide better joint stability. Optimally adjusting the co-activation ratio of these muscle groups effect the outcome of the selected injury biomarkers. For example, increasing quadriceps to hamstring ratio decreases hip abduction angle reduces chances of ACL injury.

In an embodiment, the system 300 designs a plurality of such neuro-muscular controllers by varying the co-activation level during the high contact type activity. From amongst the plurality of neuro-muscular controllers, the system 300 may then select a neuro-muscular controller that may be capable of generating the plurality of the optimal muscle co-activation parameters.

The system 300 selects a plurality of combinations of the plurality of muscles groups. For example, specific muscles identified may include quadriceps, hamstring and tibialis anterior and gastrocnemius. A change in activation functions of these muscle groups produce maximum detectable changes in the biomarkers selected as ACL injury predictor. Herein, from the analysis of the injury biomarkers, the injury biomarkers Hip abduction angle, knee adduction load, knee flexion and ankle inversion angle have been identified through inverse dynamics simulation of the model developed. In an embodiment, the inverse dynamic simulation may be performed by using an Inverse Dynamic (ID) tool associated with the OpenSim platform. The ID Tool determines generalized forces (e.g., net forces and torques) at the joints responsible for the contact type activity. Given the kinematics (e.g., states or motion) describing the movement of a model and perhaps a portion of the kinetics (e.g., external loads) applied to the model, the ID Tool uses these data to perform an inverse dynamic analysis. Classical mechanics mathematically expresses the mass-dependent relationship between force and acceleration, F=ma, with equations of motion. The ID tool solves these equations, in the inverse dynamics sense, to yield the net forces and torques at each joint which produce the movement.

In an embodiment, the system 300 varies activation of selected muscle groups by assigning incremental values to the co-activation ratios corresponding to a plurality of combinations of muscle groups, thereby optimally adjusting the co-activation ratio of the plurality of muscle groups. For example, the system 300 may assign incremental values to the co-activation ratios corresponding to said as combinations: combination 1: Quad:ham 0.1, TA:LG 0.2; combination 2: Quad:ham 0.1, TA:LG 0.3, and so on. For each of the plurality of combinations, the system 300.

For each selected combination, the system 300 calculates a muscle tendon dynamics using muscle characteristics and force, velocity relation. Thereafter, the system 300 computes multibody dynamic equation and derives the kinematic parameters (including acceleration, velocity and position) that the simulated model needs to follow for the calculated muscle excitation. Said calculation is termed as forward dynamics loop, as is shown and described in FIG. 4B. This loop is repetitively calculated for the plurality of combinations till the best result is obtained. Additionally, the system 300 calculates values of the plurality of injury biomarkers and compares till a set of predefined constraints are satisfied. In an embodiment, the set of predefined constraints includes hip abduction angle to be minimum, knee flexion angle to be maximum, knee abduction loading to be minimum, ankle inversion angle to be minimum. After computation of all the combinations, the combination which best matches the constraint are selected by the system as the optimal muscle co-activation parameters to avoid the predicted injury. Herein, it will be noted that the disclosed system 300 can be used to train athletes or to prepare therapy regiments to avoid or rehabilitate from injuries.

In an embodiment, the system 300 includes a real time biofeedback module, based on observations done on sensing (motion parameters and EMG signals), to minimize the error between simulated movement and actual movement of the subject. For example, in case best result for a subject is obtained at a combination of Quad:ham activation 0.3, Ta:LG activation: 0.2, then said values can be considered as final output of the system 300. Depending upon said values, specific training can be registered for the subject, so that the activation function is controlled and risk of injury is reduced. In an embodiment, the system 300 may provide the plurality of optimal muscle co-activation parameters to the musculoskeletal model. The musculoskeletal model may re-simulate the plurality of contact type activities based on the plurality of optimal muscle co-activation parameters. An example process flow for injury risk prediction and corresponding corrective action for high contact type activity is further described with reference to FIGS. 4A and 4B.

Figure 4A:
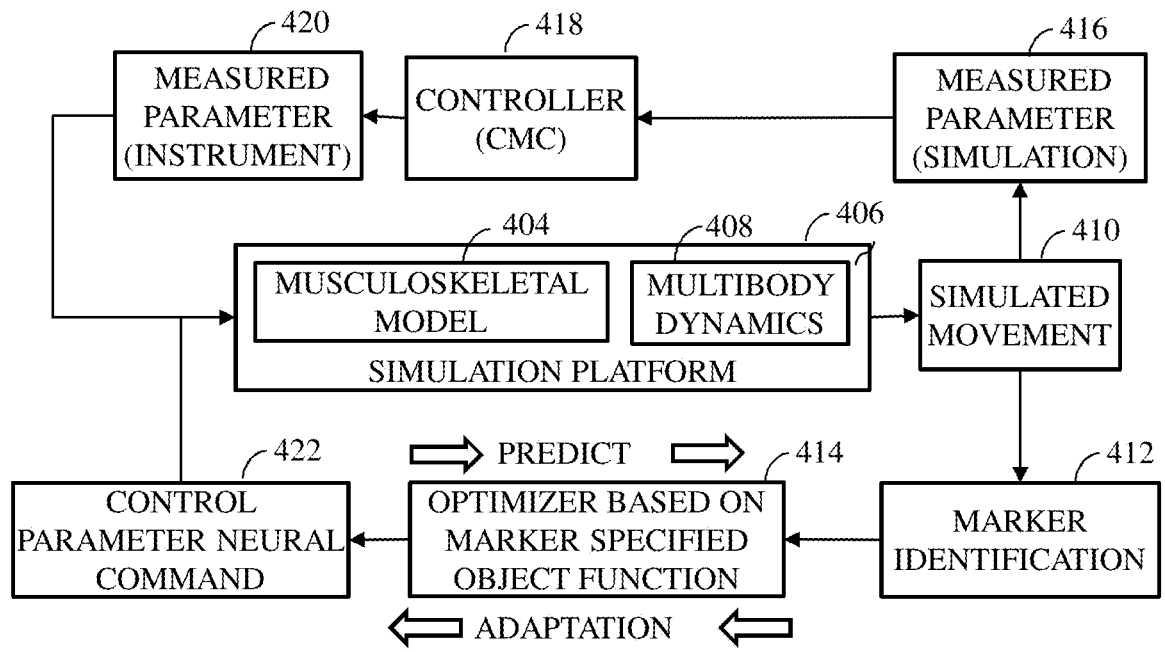
FIG. 4A illustrates an example process flow for injury risk prediction and corresponding corrective action for high contact type activity, in accordance with an embodiment of the present subject matter.

FIG. 4A illustrates a process flow 400 for injury risk prediction and corresponding corrective action for high contact type activity, in accordance with an example embodiment. The disclosed method predicts risk of injury during contact type activity such as a high fall scenario performed by a subject (for example, a sports person), and subsequently generates a corrective model, which can be used to retrain the muscles and reduce the chances of injury to the subject.

In an embodiment, the process flow 400 is initiated by generating a simulation platform 402 including a full body musculoskeletal model 404 at 406. Accordingly, said simulation platform 402 includes the developed musculoskeletal model 404 along with a multibody dynamics engine 408, inherent to OpenSim™ software. The musculoskeletal model 404 along with the multibody dynamics 408 constitutes the simulation platform 402. Said simulation platform 402 is used to simulate any particular ambulatory activity or exercise. The developed musculoskeletal model 404 is simulated to jump (for example, a single leg drop jump as illustrated in FIGS. 1A-1D) from various different heights, ranging from 40 to 100 cm on a solid platform at 410. Unsupervised and sudden jump from such heights may cause tear in the ACL ligament. Herein, purpose of the simulation by the simulation platform 402 is to induce an injury scenario.

An improvement of the disclosed musculoskeletal model as compared to the conventional models is in terms of ligament placement and a modified 3DoF knee to facilitate sliding motion. In an embodiment, a group of 9 different ligaments naming, ACL (anterior and posterior), PCL (anterior and posterior), Fibular Collateral ligament (lateral), Patella-femoral ligament and Tibial collateral ligament (anterior, intermediate and posterior) are modelled to depict the knee and ankle joint behaviour during the contact type activity such as ACL injury.

Weather an injury has occurred or not is reflected by one or more injury biomarkers. Said injury biomarkers are calculated from forward and inverse dynamics, as will be explained further. Using the inverse dynamics simulation of the musculoskeletal model, one or more injury biomarkers including, but not limited to, hip abduction angle, knee adduction load, knee flexion and ankle inversion angle are identified at 412. Herein, for the purpose of experimentation, ratio of specific muscle groups to be controlled, are identified. Examples of said muscle group's ratios include, but are not limited to, quadriceps-hamstring ratio and tibialis anterior-gastrocnemius ratio. It will be understood that a change activation function of said muscle groups produce a substantial (or maximum) detectable changes in the injury biomarkers selected as ACL injury predictor.

The one or more injury biomarkers are analyzed to check whether there is any chance of ACL injury, incurred from the jump. In an embodiment, the one or more injury biomarkers are analysed in OpenSim platform. Once the musculoskeletal model predicts chances of injury, calculated with respect to said injury biomarkers, a neuro-muscular controller is designed at 414, which facilitates in adapting and/or preventing the predicted injury. Herein, it will be understood that adaptation to prevent injury is based on the concept of muscle synergy.

Different muscle characteristics may be compared based on varying the level of co-activation of participating muscle groups. In an embodiment, the muscle co-activation and synergy of two groups of muscle are adjusted. In an example embodiment, said muscle groups include, but are not limited to, Quadriceps: hamstring and gastrocnemius: Tibilias Anterior. Optimally adjusting the co-activation ratio of these muscle groups effect the outcome of the selected injury biomarkers. For example, increasing quadriceps to hamstring ratio decreases hip abduction angle, which in turn, reduces chances of ACL injury.

In an embodiment, the co-activation ratio of muscle groups are optimally selected to best select a neuro-muscular controller from amongst a plurality of neuro-muscular controllers, which can provide chances of injury reduction to the predicted injury model. In an example embodiment, three such neuro-muscular controllers are designed, by varying the co-activation level during the high contact activity, for example drop jump activity. From the different possible combinations, the optimal controller is selected to facilitate adjustments to avoid the predicted injury. An example of optimally selecting the neuro-muscular controller is described further with reference to FIG. 4B.

Figure 4B:
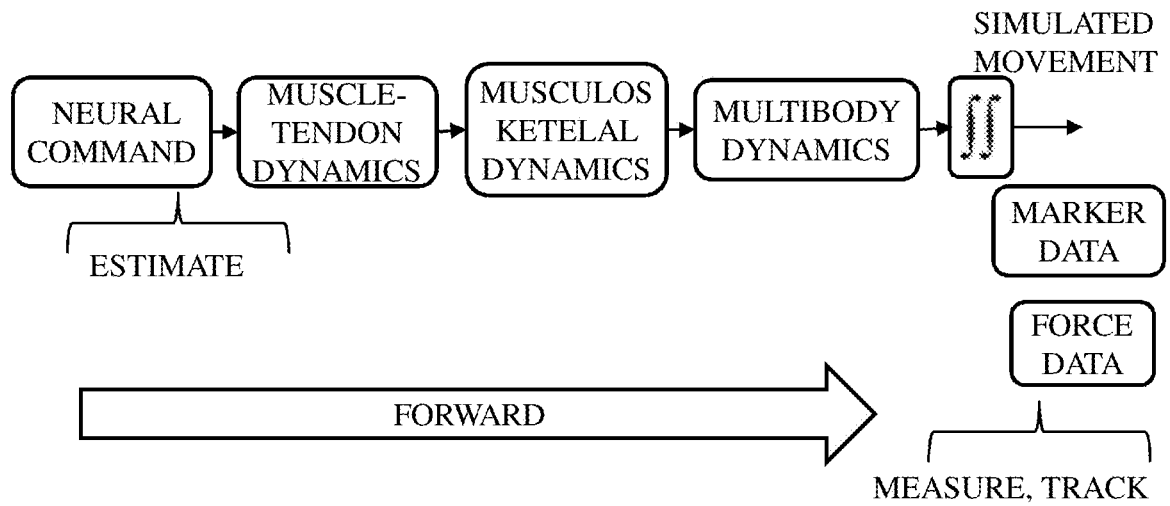
FIG. 4B illustrates an example process flow for determining corrective action for a predicted injury risk pertaining to a high contact activity, in accordance with an example embodiment of the present subject matter.

Referring now to FIG. 4B an example process flow 450 for optimally selecting the neuro-muscular controller is described in accordance with an example embodiment. In the present example, four muscles have been selected and including the Quadriceps: hamstring and gastrocnemius: Tibilias Anterior. Muscle co-activation and synergy of two groups of muscle are adjusted to effect the outcome of the selected injury biomarkers. In an example implementation, activation of the selected muscles can vary from 0 to 1, precision step being 0.1. So, in incremental steps of 0.1, 0.2, and so on, activation for all these muscle are varied in 10 steps. For aforementioned four muscles, grouped in pair (for example, a pair of Quadriceps: hamstring and a pair of gastrocnemius: Tibilias Anterior muscles), around ninety different possible combinations are obtained. For instance, combination 1: Quadriceps:hamstring 0.1, gastrocnemius:Tibilias Anterior 0.2; Combination 2: Quadriceps:hamstring 0.1, gastrocnemius:Tibilias Anterior 0.3, and so on.

For each of the selected combinations, the neuro-muscular controller calculates the muscle tendon dynamics using muscle characteristics and force, velocity relation at 452. Further, the neuro-muscular controller computes multibody dynamic equation and derives the kinematic parameters (acceleration, velocity and position) that the simulated model needs to follow for the calculated muscle excitation. Said calculation is termed as forward dynamics loop, as shown in FIG. 4B. The loop is repetitively calculated for all combination till the best result is obtained. The forward dynamic loop is explained further in description below.

In forward dynamics, a mathematical model describes how coordinates and their velocities change due to applied forces and torques (moments). From Newton's second law, it can be described that the accelerations (rate of change of velocities) of the coordinates in terms of the inertia and forces applied on the skeleton as a set of rigid-bodies:

$$\ddot{q}=[M(q)]\tau+C\{q,\dot{q}\}+G(q)+F\}$$

where $\ddot{q}$ is the coordinate accelerations due to joint torques, $\tau$, Coriolis and centrifugal forces, C(q,$\dot{q}$), as a function of coordinates, q, and their velocities, $\dot{q}$, gravity, G(q), and other forces applied to the model, F, and C(q,$\dot{q}$) [M(q)] is the inverse of the mass matrix $\tau_m$=[R(q)]f(a,l,l) moment due to muscle force, $\dot{l}$=$\Lambda$(a,l,q,$\dot{q}$) muscle contraction dynamics.

$\dot{a}$=A(a,x) muscle activation dynamics.

The net muscle moments, $\tau_m$, in turn, are a result of the moment arms, R(q), multiplied by muscle forces, f, which are a function of muscle activations, a, and muscle fiber lengths, l, and velocities, $\dot{l}$.

Muscle fiber velocities are governed by muscle contraction dynamics, $\Lambda$, which is dependent on the current muscle activations and fiber lengths as well as the coordinates and their velocities. Activation dynamics, A, describes how the activation rates, $\dot{a}$, of the muscles respond to input neural excitations, x, generally termed the model's controls. These form a set of differential equations that model musculoskeletal dynamics. Muscle force and muscle activations are based on a Hill type muscle model, used in Opensim which correlates muscle activation with muscle force or torque.

The force-producing properties of muscle are complex and for simplicity, lumped-parameter, dimensionless muscle models, capable of representing a range of muscles with different architectures, are most commonly used in the dynamic simulation of movement. In a complex musculoskeletal model, the model can be actuated by 50 or more muscle-tendon units, each of which is represented as a Hill-type contractile element in series with a tendon.

The 'thelen model' (Model used in OpenSim™) uses a standard equilibrium muscle model based on the Hill model. The muscle-tendon complex consists of three components: a contractile element (CE), a parallel element (PE), and a series element (SE). The muscle force generated is a function of three factors: the activation value (a), the normalized length of the muscle unit, and the normalized velocity of the muscle unit. The functions describing the force generated by a muscle as its length varies are called the active length curve (AL) for the contractile element and the passive length curve (PL) for the parallel element.

The parameters used to characterize each muscle are maximum isometric force, optimal muscle fiber length, tendon slack length, maximum contraction velocity, and pennation angle. During a forward dynamic simulation, the muscle force is calculated using two states: the activation value and the muscle fiber length.

Musculoskeletal dynamics equations are solved using $5^{th}$ order Runge Kutta Feldberg integrator. The integrator applies muscle actuator as the force/torque supply and calculates a defined trajectory of motion, based on which, the kinematic parameters are calculated.

Referring back to FIG. 4A, the method incorporates a feedback loop, where the outputs of the neuro-muscular controller at 414 is introduced in the simulation platform 402 and the simulation platform 402 is again simulated with the predefined high contact level activity. Depending upon the control action of the neuro-muscular controller at 414, injury risks can be lowered due to muscular adaptation to prevent the injury. In an embodiment, the total simulation model can be validated with actual data (without inducing injury condition) for proper calibration of the model. For this purpose, joint kinematic and kinetic data are measured from a subject at 420 and fitted to OpenSim model. OpenSim recalculates the system dynamics and muscle activation using the in-build Computed muscle control (CMC) block 418. Muscle conditions adapted by the controller can be used to train athletes to reduce chances of such injury. This methodology can also be used extensively in therapy planning and rehabilitation training. In an embodiment, the method may include providing real time biofeedback at 422 based on observations done on sensing (motion parameters and EMG signals), to minimize the error between simulated movement and actual movement of the subject.

Figure 5:
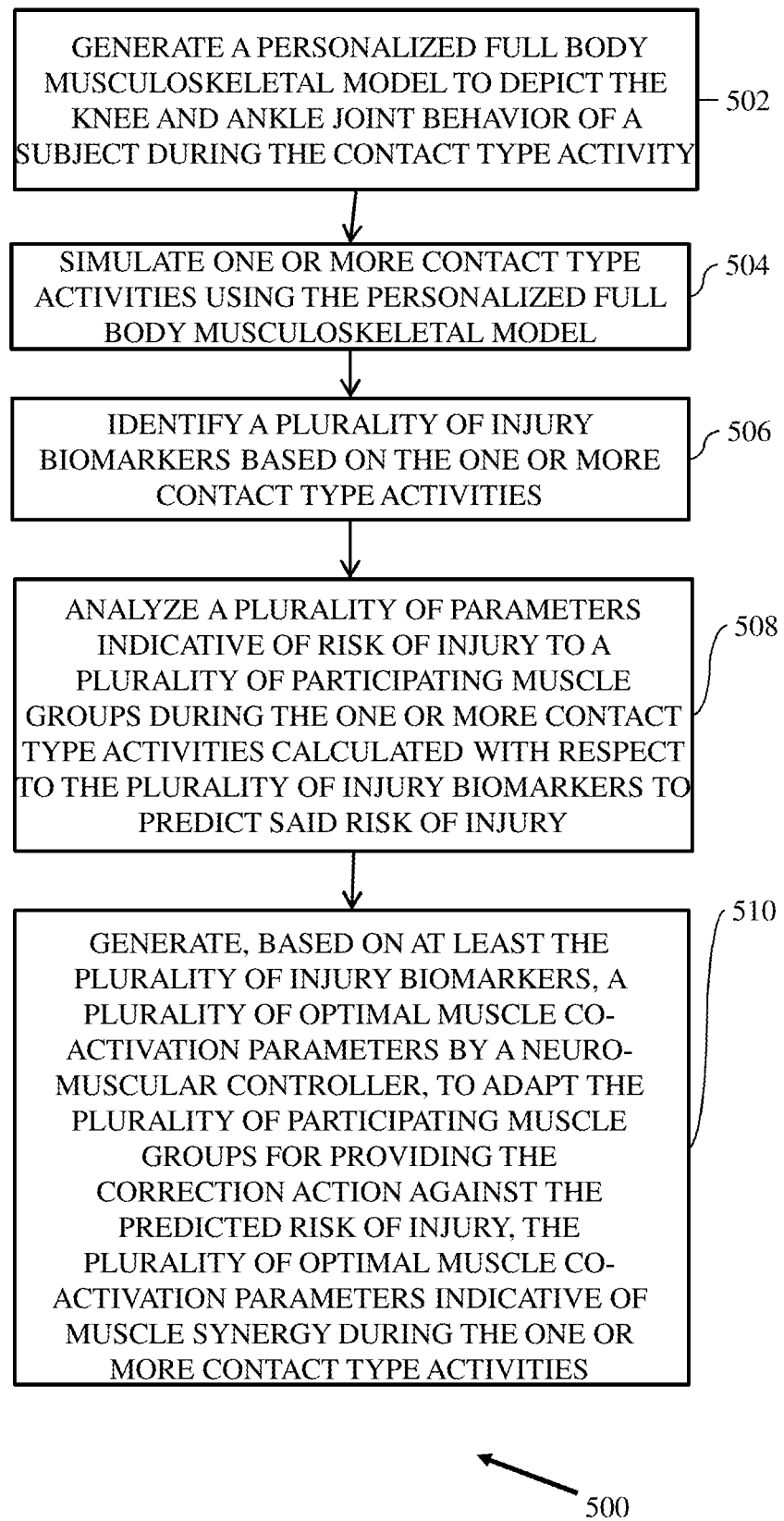
FIG. 5 illustrates an example flow diagram representing a method for injury risk prediction and corresponding corrective action for high contact type activity, in accordance with an example embodiment of the present subject matter.

FIG. 5 illustrates a flow diagram of a method 500 for risk prediction and corrective action for a contact type activity, according to some embodiments of the present disclosure. The method 800 may be described in the general context of computer executable instructions. Generally, computer executable instructions can include routines, programs, objects, components, data structures, procedures, modules, functions, etc., that perform particular functions or implement particular abstract data types. The method 500 may also be practiced in a distributed computing environment where functions are performed by remote processing devices that are linked through a communication network. The order in which the method 500 is described is not intended to be construed as a limitation, and any number of the described method blocks can be combined in any order to implement the method 500, or an alternative method. Furthermore, the method 500 can be implemented in any suitable hardware, software, firmware, or combination thereof. In an embodiment, the method 500 depicted in the flow chart may be executed by a system, for example, the system 202 of FIG.

2. In an example embodiment, the system 202 may be embodied in an exemplary computer system.

Referring to FIG. 5, in the illustrated embodiment, the method 500 is initiated when at 502, the method 500 includes generating a personalized full body musculoskeletal model to depict the knee and ankle joint behaviour of a subject during the contact type activity. An example of the personalized full body musculoskeletal model is illustrated and described with reference to FIG. 1A. At 504, the method 500 includes simulating a plurality of contact type activities using the personalized full body musculoskeletal model. At 506, the method 500 includes identifying a plurality of injury biomarkers based on the plurality of contact type activities. At 508, the method 500 includes analyzing a plurality of parameters indicative of risk of injury to a plurality of participating muscle groups during contact type activity calculated with respect to the plurality of injury biomarkers to predict said risk of injury. At 510, the method 500 includes generating, based on at least the plurality of injury biomarkers, a plurality of optimal muscle co-activation parameters by a neuro-muscular controller, to adapt the plurality of participating muscle groups for providing the correction action against the predicted risk of injury. The plurality of optimal muscle co-activation parameters are indicative of muscle synergy during the contact type activity.

Figure 6A:
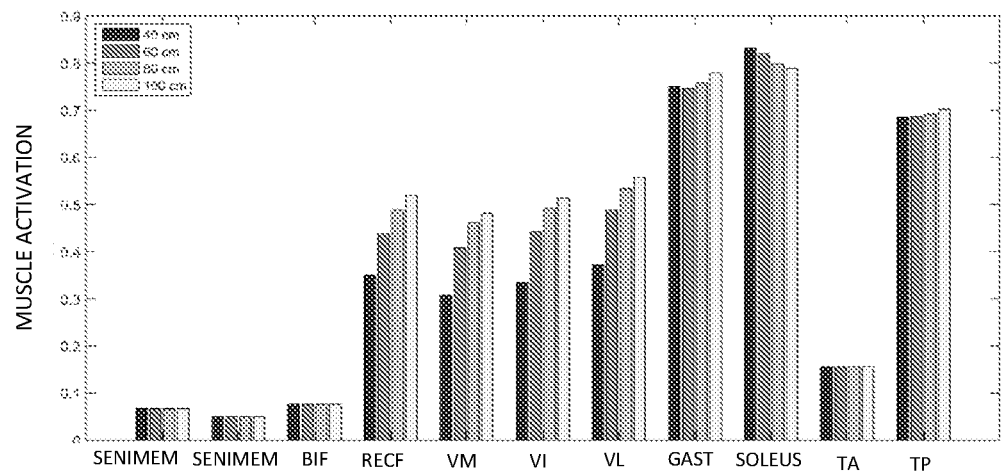
FIGS. 6A-6C illustrates experimental results for observation of the muscle activity, joint kinetics and kinematics, in accordance with an example embodiment.
Figure 6B:
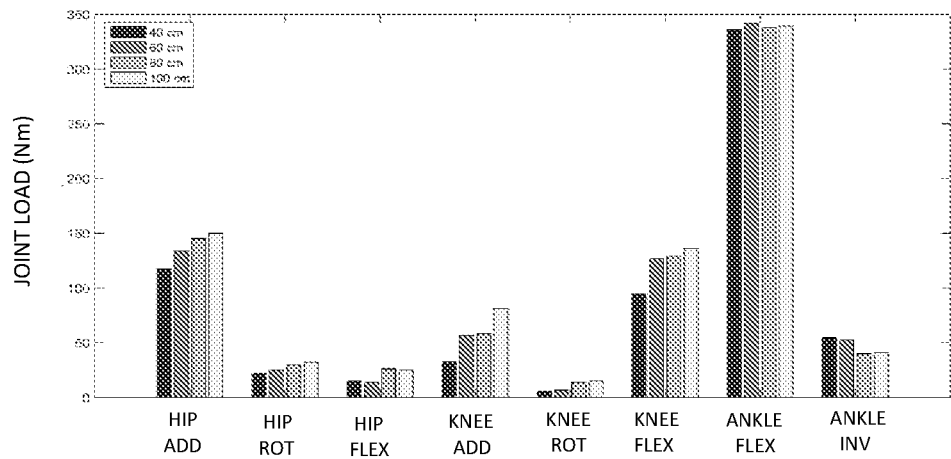
Figure 6C:
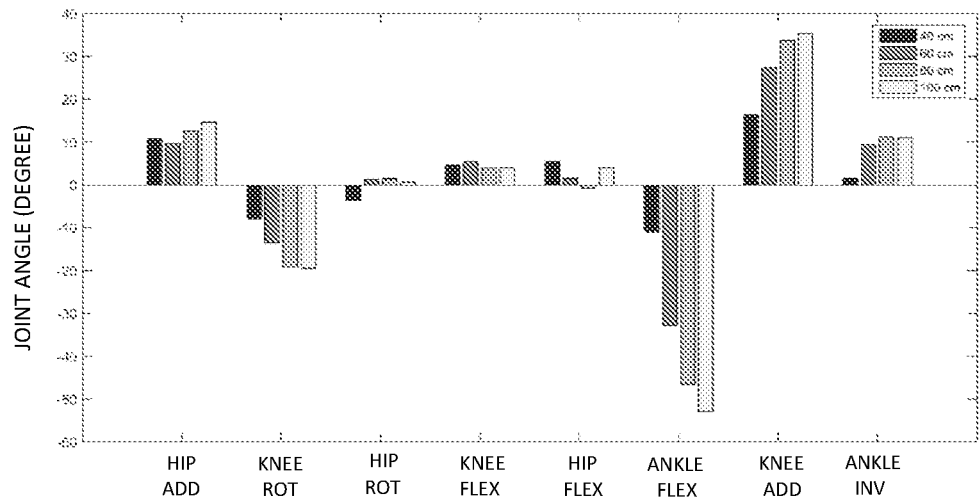

FIGS. 6A-6C illustrates experimental results for observation of the muscle activity, joint kinetics and kinematics, in accordance with an example embodiment. FIG. 6A illustrates muscle activity of nine sets of muscles including emimembranosus, semitendinosus, bicep femoris, rectus femoris, Vastus Medialis, Vastus Intermediaries, Vastus Lateralis, Gastrocnemius, Soleus, Tibilias Anterior and Tibilias Posterior during a drop jump activity from four different heights. FIG. 6B illustrates Joint kinetics including Hip adduction, rotation, flexion, Knee Adduction, rotation, flexion, Ankle flexion, and inversion during drop jump activity from four different heights. FIG. 6C illustrate Joint kinematics including Hip adduction, rotation, flexion, Knee Adduction, rotation, flexion, Ankle flexion, and inversion during drop jump activity from four different heights. It will be noted that the terminology Adduction, flexion, inversion, and rotation have been referred to as 'add', 'flex', 'inv' and 'rot', respectively in FIGS. 6B-6C. Based on the observation of the muscle activity, joint kinetics and kinematics, illustrated in FIGS. 6A-6C, a plurality of injury biomarkers are identified. ACL injury is indicated by:

Increased knee Valgus, approximated from hip adduction angle range (above 11 degree corresponds to increased chance of injury)
Increased Knee Abduction Loading
Decreased knee flexion
Increased ankle inversion for ankle sprain during drop jump Major cause of ACL injury is the high activation of Quadriceps group of muscles and relative inactivity of Hamstring group of Muscles. Gastronomies muscles are antagonist of ACL, higher activation leads to ACL injury. ACL injury can thus be reduced by increasing the activity of Hamstring group of muscles, decreasing Gastronomies activation and increased Soleus activation.

In an experiment, three neuro-muscular controllers are designed based on varying co-activation of Quadriceps-Hamstring (QH) ratio and Gastrocnemius-Tibialis Anterior (GTA) ratio. Synergistic muscle activation based neuro-muscular controller design adjusts level of activation, adapting to a better neuro-muscular control to prevent injury.

Model 1: Default action;
Model 2: Controller with constant activation of 0.1 to hamstring group and TA,
Model 3: Controller with constant activation factor of 0.2 to hamstring group and TA;
Model 4: Controller with constant activation factor of 0.3 to hamstring group and TA.

Figure 7A:
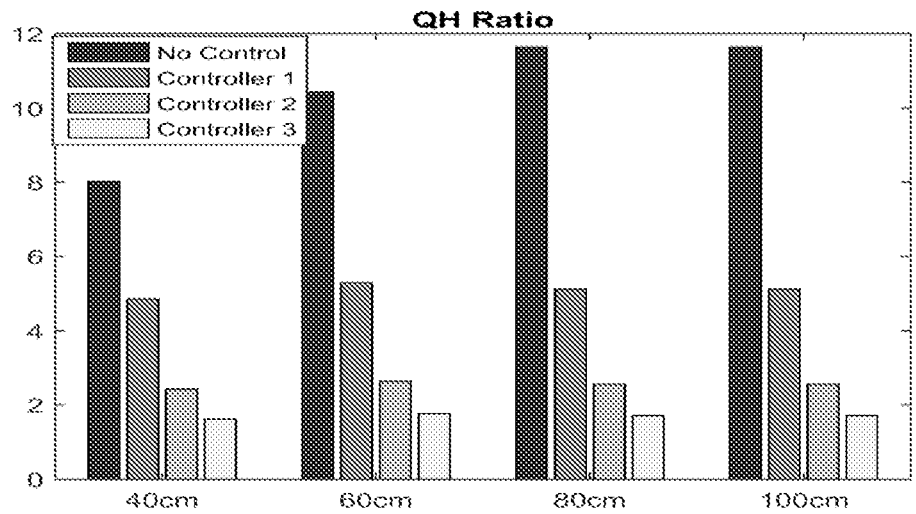
FIGS. 7A-7B illustrates controller response in terms of joint kinematics and kinetics to determine the optimal neuro-muscular controller selection, in accordance with an example embodiment.
Figure 7B:
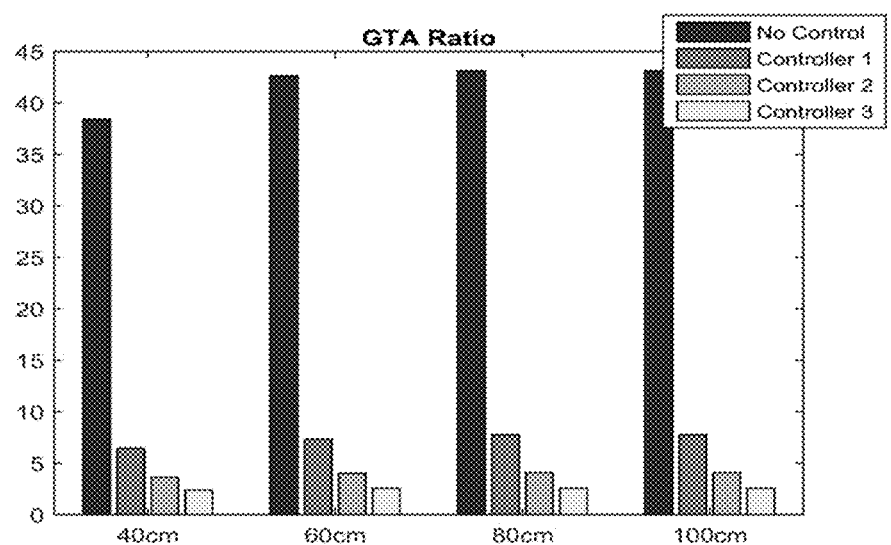

The Controller response in terms of joint kinematics and Kinetics is analyzed to determine the optimal controller selection, as is illustrated further in FIGS. 7A-7B.

Figure 8A:
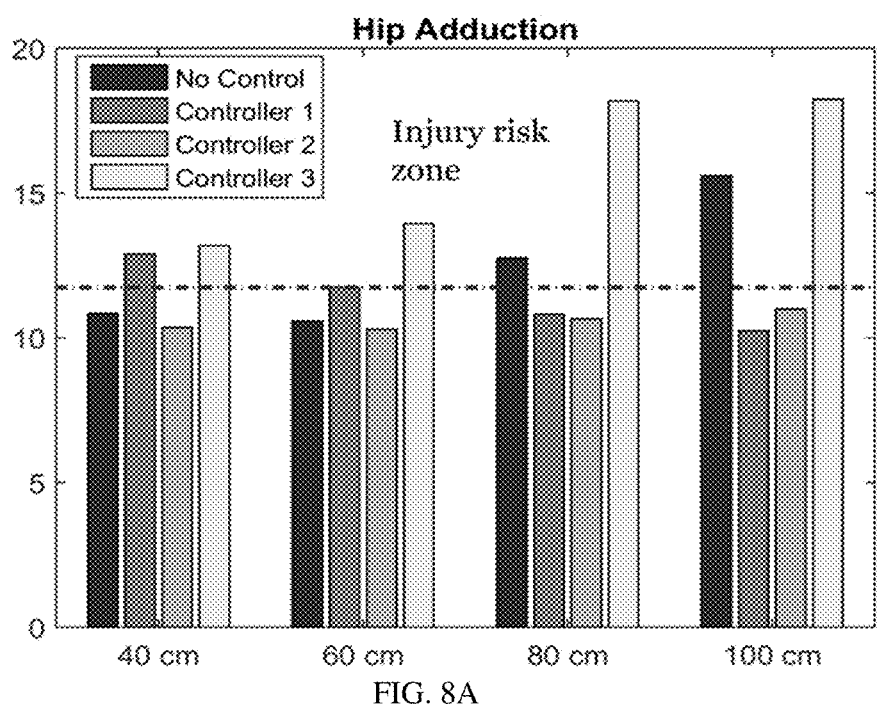
FIGS. 8A-8C illustrates controller response to injury biomarkers, in accordance with an example embodiment.
Figure 8B:
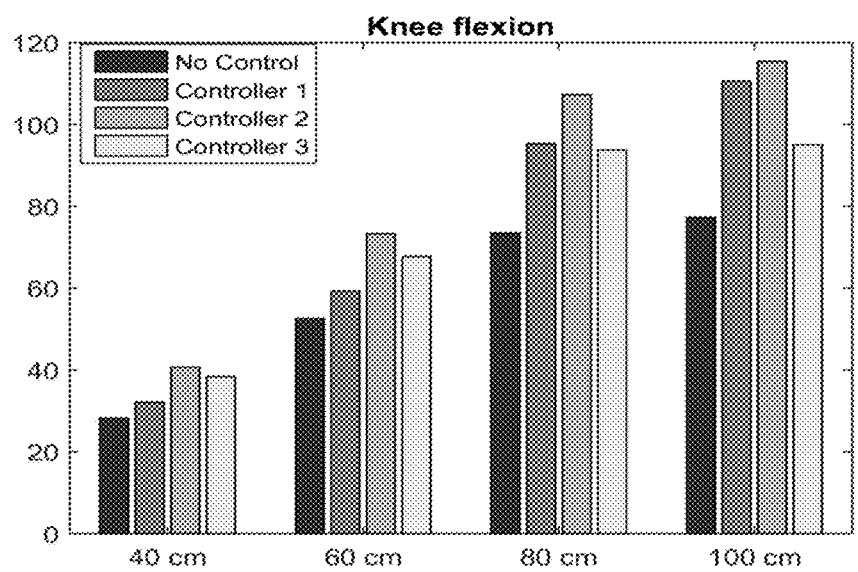
Figure 8C:
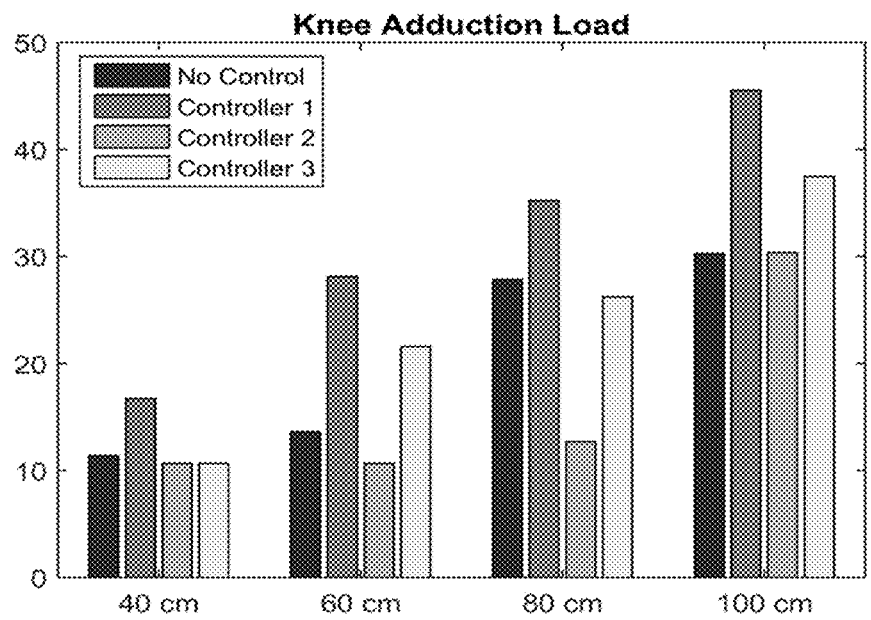

FIGS. 8A-8C illustrates controller response to injury biomarkers, in accordance with an example embodiment. Herein, the desired trend is low hip adduction angle (less than 12 degree) illustrated in FIG. 8A, high knee flexion illustrated in FIG. 8B and low knee joint loading illustrated in FIG. 8C.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

We claim:

1. A processor-implemented method for risk prediction and corrective action for a contact type activity, the method comprising:
generating a personalized full body musculoskeletal model to depict a knee and ankle joint behavior of a subject during the contact type activity, via one or more hardware processors;
simulating one or more contact type activities using the personalized full body musculoskeletal model, via the one or more hardware processors;
identifying a plurality of injury biomarkers based on the one or more contact type activities, via the one or more hardware processors;
analyzing, via the one or more hardware processors, a plurality of parameters indicative of risk of injury to a plurality of participating muscle groups during the one or more contact type activities calculated with respect to the plurality of injury biomarkers to predict said risk of injury;
generating, based on at least the plurality of injury biomarkers, a plurality of optimal muscle co-activation parameters by a neuro-muscular controller via the one or more hardware processors, to adapt the plurality of participating muscle groups for providing the correct action against the risk of injury being predicted, the plurality of optimal muscle co-activation parameters indicative of muscle synergy during the one or more contact type activities;

calculating values of the plurality of injury biomarkers for a plurality of combinations and comparing till a set of predefined constraints are satisfied, wherein the set of predefined constraints comprises: hip abduction angle be minimum, knee flexion angle be maximum, knee abduction loading be minimum, and ankle inversion angle be minimum, and wherein the set of predefined constraints follows an order of priority comprising the hip abduction angle being at highest priority, followed by knee loading, followed by knee flexion, followed by ankle inversion; and determining, based on the set of predefined constraints, a combination of the plurality of combinations as the optimal muscle co-activation parameters.

2. The method as claimed in claim 1, wherein the personalized full body musculoskeletal model comprises a 92 muscle actuators, a 3 degrees of freedom (DoF) knee with ligament connectivity, and 9 ligament bundles designed and placed with respect to anatomical constraints and bounds of the subject.

3. The method as claimed in claim 1, wherein the plurality of injury biomarkers comprises the hip abduction angle, knee adduction load, the knee flexion and ankle inversion angle.

4. The method as claimed in claim 1, wherein the plurality of participating muscles groups comprises quadriceps Hamstring, and Tibialis anterior and Gastrocnemius, wherein a change in a co-activation ratio of the plurality of participating muscles groups produce detectable changes in the plurality of injury biomarkers.

5. The method as claimed in claim 1, wherein the plurality of injury biomarkers are identified through inverse dynamics simulation of the personalized full body musculoskeletal model.

6. The method as claimed in claim 1, wherein the plurality of parameters are indicative of the risk of injury comprises muscle condition, joint kinematics and kinetics associated with said risk.

7. The method as claimed in claim 1, wherein the step of calculating values of the plurality of injury biomarkers is preceded by:

designing a plurality of neuro-muscular controllers by varying co-activation ratios associated with the plurality of participating muscle groups during the contact type activity; and selecting, from the plurality of neuro-muscular controllers, the neuro-muscular controller capable of generating the plurality of optimal muscle co-activation parameters, wherein selecting the neuro-muscular controller comprises, performing for each of the plurality of neuro-muscular controllers:

optimally adjusting the co-activation ratios of the plurality of participating muscle groups by assigning incremental values to the co-activation ratios corresponding to the plurality of combinations of the plurality of participating muscles groups;

performing, for the plurality of combinations:

calculating a muscle tendon dynamics using muscle characteristics and force, velocity relation, computing multibody dynamic equation and deriving kinematic parameters, the kinematic parameters comprising acceleration, velocity and position.

8. A system for risk prediction and corrective action for a contact type activity, the system comprising:

one or more memories; and one or more hardware processors, the one or more memories coupled to the one or more hardware processors, wherein the one or more hardware processors are capable of executing programmed instructions stored in the one or more memories to:

generate a personalized full body musculoskeletal model to depict a knee and ankle joint behavior of a subject during the contact type activity;

simulate one or more contact type activities using the personalized full body musculoskeletal model;

identify a plurality of injury biomarkers based on the one or more contact type activities;

analyze a plurality of parameters indicative of risk of injury to a plurality of participating muscle groups during the one or more contact type activities calculated with respect to the plurality of injury biomarkers to predict said risk of injury;

generate, based on at least the plurality of injury biomarkers, a plurality of optimal muscle co-activation parameters by a neuro-muscular controller, to adapt the plurality of participating muscle groups for providing the correct action against the risk of injury being predicted, the plurality of optimal muscle co-activation parameters indicative of muscle synergy during the one or more contact type activities;

calculate values of the plurality of injury biomarkers for a plurality of combinations and comparing till a set of predefined constraints are satisfied, wherein the set of predefined constraints comprises: hip abduction angle be minimum, knee flexion angle be maximum, knee abduction loading be minimum, and ankle inversion angle be minimum, and wherein the set of predefined constraints follows an order of priority comprising the hip abduction angle being at highest priority, followed by knee loading, followed by knee flexion, followed by ankle inversion; and determine, based on the set of predefined constraints, a combination of the plurality of combinations as the optimal muscle co-activation parameters.

9. The system as claimed in claim 8, wherein the personalized full body musculoskeletal model comprises a 92 muscle actuators, a 3 degrees of freedom (DoF) knee with ligament connectivity, and 9 ligament bundles designed and placed with respect to anatomical constraints and bounds of the subject.

10. The system as claimed in claim 8, wherein the plurality of injury biomarkers comprises the hip abduction angle, knee adduction load, the knee flexion and ankle inversion angle.

11. The system as claimed in claim 8, wherein the plurality of participating muscles groups comprises quadriceps Hamstring, and Tibialis anterior and Gastrocnemius, wherein a change in a co-activation ratio of the plurality of participating muscles groups produce detectable changes in the plurality of injury biomarkers.

12. The system as claimed in claim 8, wherein the plurality of injury biomarkers are identified through inverse dynamics simulation of the personalized full body musculoskeletal model.

13. The system as claimed in claim 8, wherein the plurality of parameters are indicative of the risk of injury comprises muscle condition, joint kinematics and kinetics associated with said risk.

14. The system as claimed in claim 8, wherein the step of calculating values of the plurality of injury biomarkers is preceded by:
  design a plurality of neuro-muscular controllers by varying co-activation ratios associated with the plurality of participating muscle groups during the contact type activity; and
  select, from the plurality of neuro-muscular controllers, the neuro-muscular controller capable of generating the plurality of optimal muscle co-activation parameters, wherein selecting the neuro-muscular controller comprises, performing for each of the plurality of neuro-muscular controllers:
    optimally adjust the co-activation ratios of the plurality of participating muscle groups by assigning incremental values to the co-activation ratios corresponding to the plurality of combinations of the plurality of participating muscles groups, and for the plurality of combinations, performing:
      calculate a muscle tendon dynamics using muscle characteristics and force, velocity relation,
      compute multibody dynamic equation and deriving kinematic parameters, the kinematic parameters comprising acceleration, velocity and position.

15. One or more non-transitory machine readable information storage mediums comprising one or more instructions which when executed by one or more hardware processors causes the one or more hardware processor to perform a method for risk prediction and corrective action for a contact type activity, said method comprising:
  generating a personalized full body musculoskeletal model to depict a knee and ankle joint behavior of a subject during the contact type activity, via one or more hardware processors;
  simulating one or more contact type activities using the personalized full body musculoskeletal model, via the one or more hardware processors;
  identifying a plurality of injury biomarkers based on the one or more contact type activities, via the one or more hardware processors;
  analyzing, via the one or more hardware processors, a plurality of parameters indicative of risk of injury to a plurality of participating muscle groups during the one or more contact type activities calculated with respect to the plurality of injury biomarkers to predict said risk of injury;
  generating, based on at least the plurality of injury biomarkers, a plurality of optimal muscle co-activation parameters by a neuro-muscular controller via the one or more hardware processors, to adapt the plurality of participating muscle groups for providing the correct action against the risk of injury being predicted, the plurality of optimal muscle co-activation parameters indicative of muscle synergy during the one or more contact type activities;
  calculating values of the plurality of injury biomarkers for a plurality of combinations and comparing till a set of predefined constraints are satisfied, wherein the set of predefined constraints comprises: hip abduction angle be minimum, knee flexion angle be maximum, knee abduction loading be minimum, and ankle inversion angle be minimum, and wherein the set of predefined constraints follows an order of priority comprising the hip abduction angle being at highest priority, followed by knee loading, followed by knee flexion, followed by ankle inversion; and
  determining, based on the set of predefined constraints, a combination of the plurality of combinations as the optimal muscle co-activation parameters.

16. The one or more non-transitory machine readable information storage mediums of claim 15, wherein the personalized full body musculoskeletal model comprises a 92 muscle actuators, a 3 degrees of freedom (DoF) knee with ligament connectivity, and 9 ligament bundles designed and placed with respect to anatomical constraints and bounds of the subject.

* * * * *